United States Patent [19]

Oki et al.

[11] 4,337,312
[45] Jun. 29, 1982

[54] PROCESS FOR PRODUCING ANTHRACYCLINE GLYCOSIDES

[75] Inventors: Toshikazu Oki, Yokohama; Akihiro Yoshimoto, Fujisawa; Kageaki Kouno, Tokyo; Taiji Inui, Chigasaki; Tomio Takeuchi; Hamao Umezawa, both of Tokyo, all of Japan

[73] Assignee: Sanraku-Ocean Co., Ltd., Tokyo, Japan

[21] Appl. No.: 181,545

[22] Filed: Aug. 26, 1980

[30] Foreign Application Priority Data

Sep. 7, 1979 [JP] Japan ............................... 54-115521

[51] Int. Cl.³ ............................................. C12P 19/56
[52] U.S. Cl. ....................................... 435/78; 435/172
[58] Field of Search ........................................... 435/78

[56] References Cited

U.S. PATENT DOCUMENTS

| 3,590,028 | 6/1971 | Arcamone et al. | 435/78 |
| 3,875,010 | 4/1975 | Mancy et al. | 435/78 |
| 4,147,778 | 4/1979 | Umezawa et al. | 435/78 |

*Primary Examiner*—Alvin E. Tanenholtz
*Attorney, Agent, or Firm*—Jordan and Hamburg

[57] ABSTRACT

The invention is to provide a new process for producing daunomycin and baumycins having potent antitumor activity and low toxicity by microbial conversion of anthracyclinones such as aklavinone and $\epsilon$-rhodomycinone.

7 Claims, No Drawings

PROCESS FOR PRODUCING ANTHRACYCLINE GLYCOSIDES

BACKGROUND OF THE INVENTION (1) Field of the Invention

The present invention relates to a process for producing daunomycin and baumycins, and more particularly, the present invention relates to a process for producing anthracycline glycosides of the general formula I:

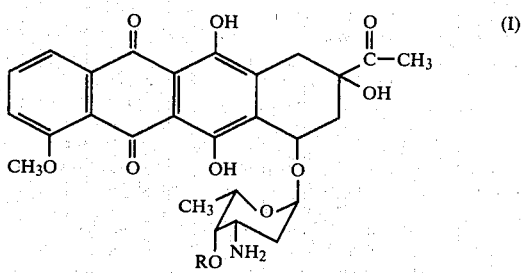

wherein

R represents a hydrogen atom or the following structure:

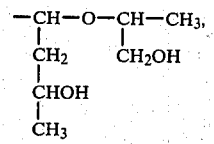

by microbial conversion of anthracyclinones having the general formula II:

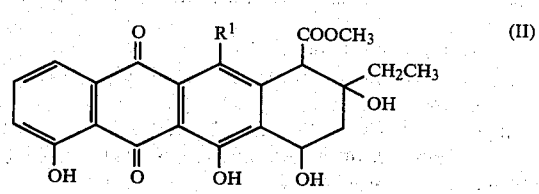

wherein $R^1$ represents a hydrogen atom or a hydroxyl group, using daunomycin- or baumycin-producing microorganisms and mutants therefrom.

(2) Description of the Prior Art

A number of anthracycline glycosides have been described in prior literature. Among them, daunomycin and adriamycin are particularly being watched with keen interest by those in the field of cancer chemotherapy and have already been applied clinically for human cancers. Preparation of adriamycin by fermentation of *Streptomyces peucetius var. caesius* is disclosed in U.S. Pat. No. 3,590,028. Chemical conversion of daunomycin to adriamycin is taught in U.S. Pat. No. 3,803,124. Daunomycin produced by fermentation of *S. peucetius* in U.K. Pat. No. 1,003,383 is the same as Rhone-Poulenc's 13057RP (See U.K. Pat. Nos. 985,598, 1,188,262 and 1,241,750 and U.S. Pat. No. 3,616,242) and dihydrodaunomycin is disclosed in U.S. Pat. No. 3,686,163.

Rhodomycinone, isorhodomycinone and rhodomycins-related antibiotics are described in Chem. Ber. 88, 1792-1818 (1955); Chem. Ber. 101, 1341-1348 (1968); J. Med. Chem. 20, 957-960 (1977); Pharmacie 27, 782-789 (1972); Zeit. Allg. Mikrobiol., 14, 551-558 (1974); Tetrahed. Lett. No. 38, 3699-3702 (1973); Folia Microbiol., 24, 293-295 (1979) and J. Antibiotics, 32, 420 (1979).

Aklavinone, aclacinomycins and baumycins are disclosed in U.S. Pat. No. 3,988,315, and by Oki et al in J. Antibiotics 28, 830 (1975), 32, 791-812 (1979), 30, 619-621 (1977), and 30, 622-624 (1977), and in Jap. J. Antibiotics, 30, S-70-84 (1977).

For further illustrative and summary disclosures of anthracycline antibiotics, see Index of Antibiotics from Actinomycetes, Hamao Umezawa, Editor-in-Chief, University Park Press, State College, Pa., U.S.A. (1967). The textbook, Antibiotics, Volume 1, Mechanism of Action, edited by D. Gottlieb and P. D. Shaw, Springer-Verlag, New York, Inc., N.Y. (1967) on pages 190-210 contains a review by A. DiMarco entitled Daunomycin and Related Antibiotics.

In the continuation of studies on biosynthesis of anthracycline glycosides, particularly daunomycin and adriamycin, the present inventors discovered a new biosynthetic pathway to daunomycin and have developed unique process for producing daunomycin, baumycins and their related anthracycline glycosides with high yield from biologically inactive anthracyclinones by microbial glycosidation. As a result, the present inventors found that daunomycin and related-anthracycline-producing microorganisms, for example, *Streptomyces coeruleorubidus* ME130-A4 (FERM-P 3540, ATCC 13740), *Streptomyces peucetius* subsp. *carneus* ATCC 21354, *Streptomyces peucetius* NRRL B-3826 (FERM-P 3989) and mutants therefrom, did not produce daunomycin and baumycins from daunomycinone, but did from aklavinone and ε-rhodomycinone by microbial glycosidation. The inventors, thus, first established that a biologically inactive anthracyclinone aglycone added exogenously to the culture medium is preferably converted to biologically potent anthracyclines by the use of microorganisms.

OBJECTS OF THE INVENTION

Accordingly, it is an object of this invention to provide a new process for producing anthracycline glycosides daunomycin and baumycins A1 and A2 having potent antitumor activity and low toxicity by microbial conversion of the biologically inactive anthracyclinones.

DETAILED DESCRIPTION OF THE INVENTION

The starting materials of the present invention are biologically inactive anthracyclinones such as aklavinone and ε-rhodomycinone having the formula II:

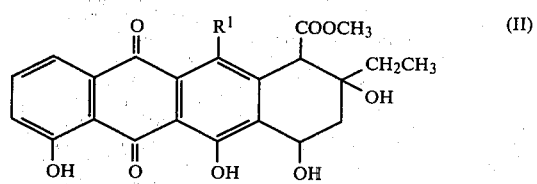

wherein $R^1$ represents a hydrogen atom to be aklavinone or a hydroxyl group to be ε-rhodomycinone. The anthracyclinones mentioned above can be isolated directly from their cultured medium or obtained by acid hydrolysis of the corresponding anthracycline glycosides, for example, from aclacinomycins A and B (U.S. Pat. No. 3,988,315). MA144 G1, G2, L, N1, S1, S2, U1, U2 (Japan Pat. Kokai No. SHO 53-44555), Aclacinomycin Y (Japan Pat. Kokai No. SHO 54-63067), and rhodomycins produced by *Actinomyces roseoviolaceus, Streptomyces purpurascens, Streptomyces coeruleorubidus* (ATCC 13740) and *Streptomyces peucetius* (NRRL B-3826).

Microorganisms used for the present invention are known daunomycin- or baumycin-producing strains such as *Streptomyces coeruleorubidus* ME130-A4 (FERM-P 3540), *Streptomyces peucetius* subsp. *carneus* ATCC 21354, *Streptomyces coeruleorubidus* ATCC 13740, *Streptomyces peucetius* NRRL B-3826 (FERM-P 3989) and various mutants therefrom obtained by the mutation techniques such as X-ray and UV irradiation, or by the mutation using chemical mutagens such as NTG (N-methyl-N'-nitro-N-nitrosoguanidine) and diepoxybutane. For example, mutant strains, 1U-222 and 1U-479 derived from *Streptomyces coeruleorubidus* ME130-A4 are incapable of producing anthracycline pigments and capable of producing anthracycline glycosides from anthracyclinones as substrate and also can be most preferably used for the present invention.

Among the mutant strains obtained, strain 1U-222 was deposited in the American Type Culture Collection, 12301 Parklawn Drive, Rockville, Md. 20852, U.S.A. and in the Fermentation Research Institute, Japan, and added to their permanent collections of microorganisms as ATCC 31670 and FERM-P 5080, respectively. The toxonomical properties were compared to those of the parent strain, *Streptomyces coeruleorubidus* ME130-A4 (FERM-P 3540, ATCC 31276), as follows:

1. Morphological characteristics:

Under microscope, open spirals and hooks in aerial mycelia are observed to develop well from branched substrate mycelia (about 1 μm in diameter) in both parent and mutant 1U-222 strains. Mature spore chain is moderately long with more than ten spores. The spores measure 0.6–0.8 × 1.0–1.2 μm, and their surface is spiny. The strains can not produce any verticillated sporophore, sporangium and sclerotium.

2. Properties on various media:

The description in parentheses follows the color standard "Color Harmony Manual" published by Container Corporation of America, U.S.A. and that of "Japan Color Institute".

| Medium | Parent strain | Mutant strain 1U-222 |
| --- | --- | --- |
| (1) Sucrose-nitrate agar (27° C.) | Growth: Abundant, light yellowish pink; aerial mycelium: almost not produced, but sometimes white mycelium without mature spore chain dotted; no soluble pigment. | Growth: Abundant, grayish yellow (3ec)- grayish yellowish pink (5ec); aerial mycelium: light gray after long period of incubation, but mature spore chain not produced; no soluble pigment. |
| (2) Glucose-aspargine agar (27° C.) | Growth: Abundant, light yellowish pink (5ca-7ca); aerial mycelium: light greenish blue (18ec); no soluble pigment. | Growth: Moderate, pale yellow (1ba) - pale orange yellow (3ca); no aerial mycelium; no soluble pigment. |
| (3) Glycerol-aspargine agar (27° C.) | Growth: Abundant, light reddish yellow-light reddish brown (5gc); aerial mycelium: light greenish blue (18ec) - pale blue (19fe); no soluble pigment. | Growth: Abundant, pale yellow (2db) - pale orange yellow (3ca); aerial mycelium: white, but mature spore chain not produced; no soluble pigment. |
| (4) Inorganic salts-starch agar (ISP medium No. 4, 27° C.) | Growth: Moderate, light yellowish pink (5ca); aerial mycelium: light greenish blue (18ec); no soluble pigment. | Growth: Abundant, pale yellow (2db) - light reddish brown (5gc); aerial mycelium: light greenish blue (18ec); no soluble pigment. |
| (5) Tyrosine agar (27° C.) | Growth: Abundant, brown - grayish yellowish brown (3ig); aerial mycelium: pale yellow green (24½dc); brown soluble pigment. | Growth: Moderate, light grayish yellowish brown (3ge) - light grayish reddish brown (5ge); no aerial mycelium; slight brown soluble pigment. |
| (6) Nutrient agar (27° C.) | Growth: Abundant, grayish yellow (3ec); aerial mycelium: light gray (d), but mature spore chain not produced; brown soluble pigment. | Growth: Abundant, grayish yellow (3ec); aerial mycelium: light brownish gray (3fe), but mature spore chain not produced; brown soluble pigment. |
| (7) Yeast extract-malt extract agar (ISP medium No. 2, 27° C.) | Growth: Abundant, grayish yellow (3ec) - light grayish reddish brown (4ge); aerial mycelium: light greenish blue (18ec) - pale blue (19fe); slight soluble pigment. | Growth: Abundant, light olive brown (2ge); aerial mycelium: light greenish blue (18ec) - pale blue (19fe); slight soluble pigment. |
| (8) Oatmeal agar (ISP medium No. 3, 27° C.) | Growth: Abundant, pale yellow (2db) - grayish yellow (3ec); aerial mycelium: light gray (d); slight soluble pigment. | Growth: Abundant, pale yellow (2db); aerial mycelium: light greenish blue (18ec); no soluble pigment. |

3. Physiological properties:

(1) Growth temperature was examined on maltose-yeast extract agar (maltose 1.0%, yeast extract 0.4%, agar 3.5%, pH 6.0) at 20°, 24°, 27°, 30°, 37° and 50° C. Optimal temperature for the growth is 27° C. to 37° C., but no growth at 50° C.

(2) Gelatin liquefaction: In glucose, peptone and gelatin medium, gelatin liquefaction began around two weeks after incubation at 20° C. and was moderate.

(3) Starch hydrolysis on inorganic salts-starch agar at 27° C.: Hydrolysis was observed after 5 days incubation.

(4) Peptonization and coagulation of skim milk at 37° C.: Weak to moderate coagulation began after 7 days incubation and then weak peptonization was observed.

(5) Melanin formation in tryptone-yeast extract broth, peptone-yeast extraction agar, and tyrosine agar at 27° C.: Positive in all media.

(6) Utilization of carbohydrate in Pridham-Gottlieb basal medium at 27° C.: Abundant growth with L-arabinose, D-xylose, D-glucose, D-fructose, sucrose, inositol, L-rhamnose, raffinose and D-mannitol.

(7) Liquefaction of calcium malate in calcium malate agar at 27° C.: Strong to moderate liquefaction around the growth was observed after 3 days incubation.

(8) Nitrate reduction in peptone water containing 1% sodium nitrate (ISP medium No. 9), incubated at 27° C.: Negative. In addition, these physiological characteristics of the mutant strain 1U-222 did not differ greatly from those of the parent strain ME130-A4.

Various mutants used for the present invention can be obtained from microorganisms belonging to the genus Streptomyces by the physical treatment with irradiations such as ultraviolet, $\alpha$-, $\beta$-, $\gamma$- and X-ray, or by mutation using chemical mutagens such as NTG and diepoxy butane. As an example of obtaining a mutant strain, NTG treatment, induction, isolation and development of the mutant strain in the present invention were performed as follows:

(1) Mutation

Anthracycline pigment non-producing mutant 1U-222 was obtained from the parent strain *Streptomyces coeruleorubidus* ME130-A4 (FERM-P 3540) by the following procedure.

The spores were scratched from *St. coeruleorubidus* ME130-A4 grown at 28° C. for 1 week on a YS agar slant (0.3% yeast extract, 1.0% soluble starch, 1.5% agar, pH 7.0), and suspended in 5 ml of 0.2 M Tris-malate buffer (pH 7.5), and sonicated twice for 15 sec. (Ultra sonic disruptor, Model 1UR-200P, 20 KHz, Tomy-Seiko K. K. Japan). The spore sonicate was filtered through a sterile absorbent cotton filter tube (2.0 cm high$\times$0.8 cm in diameter), and the resulting spore suspension (4 ml, about $5\times 10^8$ spores/ml) was added to an ethanol solution of N-methyl-N'-nitro-N-nitrosoguanidine (NTG, 10 mg/ml) at the final concentration of 1 mg/ml and shaken at 30° C. for 60 min. in the dark. The killing rate was 74.5%. After centrifugation of the NTG-treated spore suspension at 300 rpm for 10 min., the spores were resuspended in 0.85% physiological saline, diluted, inoculated onto YS-agar plate (0.3% yeast extract, 1.0% soluble starch, 1.5% agar, pH 7.0) and cultivated at 28° C. for 5 days to grow colonies.

(2) Isolation of mutants

Colonies grown as described above on YS-agar plate were inoculated onto YS agar slant and cultivated at 28° C. for one week. An inoculum obtained from each slant by a platinum-loop was inoculated in 4 ml of the seed medium (1.0% yeast extract, 1.0% soluble starch, pH 7.0), and shake-cultured at 28° C. for 2 days. Two ml of the seed culture were transferred to a 250 ml-Erlenmeyer flask containing 25 ml of the sterilized production medium (4% sucrose, 2.5% soybean meal (Prorich by Ajinomoto Co., Inc.), 0.1% yeast extract, 0.25% NaCl, 0.32% $CaCO_3$, 0.0005% $CuSO_4.5H_2O$, 0.0005% $MnCl_2.4H_2O$, 0.0005% $ZnSO_4.7H_2O$, pH 7.4) and cultivated at 28° C. for 2 days on a rotary shaker. Five ml of the cultured medium were centrifuged and the resulting mycelium was extracted with 5 ml of acetone by vigorous shaking. The amount of orange pigment extracted into the acetone layer was determined as absorbance at 495 nm of daunomycinone by a spectrophotometer, and pigment non-producing colonies were selected. Then, the capability of producing anthracycline glycosides by the exogenous addition of anthracyclinones into the culture medium was examined in every pigment non-producing colony as follows:

An inoculum of a pigment non-producing strain was inoculated in the above seed medium, shake-cultured at 28° C. for 2 days, 2.5 ml of the seed culture were transferred into a 250 ml-Erlenmeyer flask containing 25 ml of the above production medium, cultivated for 72 hours at 28° C. on a rotary shaker, and then 0.5 ml of aklavinone solution (1 mg/ml in methanol, final concentration: 20 $\mu$g/ml) was added. After further 48 hrs-cultivation, 5 ml of culture were centrifuged, and the resulting mycelium was extracted with 5 ml of acetone. After concentrating the acetone layer under reduced pressure, 0.1 ml of toluene and 1 ml of 0.2 M Tris-HCl buffer (pH 7.5) were added to the concentrate, shake-mixed and the toluene layer was separated for analysis. 20 to 50 $\mu$l of the toluene layer were spotted onto a silica gel thin-layer ($F_{254}$, Merck Co.) together with authentic daunomycin, baumycins A1 and A2, and developed with a mixture of chloroform-methanol-water-acetic acid (80:20:2:0.2). Thus, the mutant strains possessing ability to produce daunomycin, baumycins A1 and A2 from anthracyclinones according to the method as mentioned above can be obtained for use in the present invention.

In the present invention, at first anthracycline non-producing mutant strains were isolated, and then, from among them, the mutants capable of producing anthracycline glycosides by glycosidation of the sugar moieties formed in the cultured medium to the exogenously added anthracyclinones as substrate were selected.

Fermentative production of daunomycin and baumycins in the present invention is carried out as follows.

The streptomyces culture, grown on YS agar slant (0.3% yeast extract, 1.0% soluble starch, 1.5% agar, pH 7.0) and stored at 6° to 7° C., was inoculated in a liquid medium consisting of starch, glucose, organic nitrogen sources, and inorganic nitrogen sources, as an example, and shake-cultured for 1 to 2 days at 25° to 32° C. to prepare the seed culture. Then, the above seed culture was inoculated with 1 to 3% in volume to an aqueous medium, for example, consisting of sucrose, glucose, soybean meal and inorganic salts, and aerobically cultivated at 25° to 32° C. for 36 to 100 hours. During cultivation, aklavinone and/or $\epsilon$-rhodomycinone at the concentration of 10 to 200 $\mu$g/ml is added as substrate to the cultured medium on the logarithmic phase of the microbial growth, and the cultivation is further continued for 18 to 72 hours to complete the microbial conversion.

Optimal conditions for microbial conversion using *Streptomyces coeruleorubidus* ME130-A4, parent strain, and ME130-A4 1U-222, anthracycline-pigment non-producing mutant, are that the cultivation was carried out for 72 hours at 28° C. in the production medium, and then 50 $\mu$g/ml of aklavinone and/or $\epsilon$-rhodomycinone solution (2 mg/ml in methanol) were added to the cultured medium. After 48 hours cultivation, 43 $\mu$g/ml of the conversion products consisted of 5 $\mu$g/ml of daunomycin, 15 $\mu$g/ml of baumycin A1 and 23 $\mu$g/ml of baumycin A2, which were accumulated; recovery yield was over 80% on the weight basis of substrate. The parent strain can accumulate only 20 $\mu$g/ml as total pigments by direct fermentation procedure. When the concentration of substrate added to the cultured medium was over 50 $\mu$g/ml, the conversion rate decreased in the case of both anthracyclinones; for example, 100 $\mu$g/ml of aklavinone made 35 $\mu$g/ml of anthracycline glycosides with only a 35% conversion rate. In the use of the parent strain capable of producing anthracycline glycosides, a substrate is preferably added at the optimal concentration of 50 $\mu$g/ml 90 hours after cultivation, and the cultivation is continued further for 48 hours. The resulting products, including daunomycin (9 $\mu$g/ml), baumycin A1 (20 $\mu$g/ml) and baumycin A2 (2.6 $\mu$g/ml) could be accumulated to the extent of 55 $\mu$g/ml on the average from both aklavinone and $\epsilon$-rhodomycinone. This was 35 $\mu$g/ml more accumulation than without feeding of substrate.

The following is provided as an example for the production of daunomycin, baumycins A1 and A2 from aklavinone and ε-rhodomycinone by known daunomycin-producing strains. The seed culture grown for 2 days was inoculated with 2% in volume to an Erlenmeyer flask containing 25 ml of the sterile production medium, and aklavinone or ε-rhodomycinone was added after cultivation for 88 hours and further cultivated for 48 hours. Production of daunomycin and baumycins A1 and A2 was compared with the control fermentation without feeding of anthracyclinone as follows:

TABLE 1

| Strain | Aglycone added (50 μg/ml) | Products (μg/ml) Daunomycin | Baumycin A1 | Baumycin A2 | Total amount (μg/ml) | % Increase |
|---|---|---|---|---|---|---|
| Streptomyces peucetius subsp. carneus ATCC 21354 | No addition | 6.4 | 3.5 | 2.4 | 12.3 | 0 |
| | Aklavinone | 15.0 | 7.4 | 4.6 | 27.0 | 220 |
| | ε-Rhodomycinone | 16.6 | 6.0 | 4.3 | 26.6 | 216 |
| Streptomyces coeruleorubidus ATCC 13740 | No addition | 3.0 | 3.8 | 9.3 | 16.1 | 0 |
| | Aklavinone | 6.3 | 7.6 | 18.5 | 32.4 | 201 |
| | ε-Rhodomycinone | 8.1 | 6.5 | 18.7 | 33.3 | 207 |
| Streptomyces peucetius NRRL B-3826 | No addition | 0 | 0 | 5.0 | 5.0 | 0 |
| | Aklavinone | 0 | 0 | 10.2 | 10.2 | 204 |
| | ε-Rhodomycinone | 0 | 0 | 11.4 | 11.4 | 228 |
| Streptomyces coeruleorubidus NRRL B-3045 | No addition | 5.6 | 5.3 | 5.4 | 16.3 | 0 |
| | Aklavinone | 12.5 | 7.4 | 13.2 | 33.1 | 203 |
| | ε-Rhodomycinone | 11.8 | 12.3 | 10.8 | 34.9 | 214 |
| Streptomyces coeruleorubidus ME130-A4 | No addition | 4.0 | 12.4 | 6.0 | 22.4 | 0 |
| | Aklavinone | 9.0 | 29.7 | 13.7 | 52.4 | 234 |
| | ε-Rhodomycinone | 7.2 | 32.2 | 11.4 | 50.8 | 227 |

As shown in Table 1, all strains produced about twice much anthracycline glycosides from 50 μg/ml of aklavinone or ε-rhodomycinone than without addition of substrate anthracyclinones.

Determination of daunomycin and baumycins A1 and A2 in the cultured medium was performed as follows: 4 ml of acetone were added to 1 ml of cultured medium and centrifuged. The acetone layer was concentrated and extracted with 1 ml of chloroform. After concentrating the resulting chloroform layer, the residue was dissolved in 0.1 ml of chloroform, and 10 μl of the solution was spotted onto a silica gel thin-layer ($F_{254}$, Merck Co.) and developed with chloroform-methanol-water-acetic acid (80:20:2:0.2). Spots of daunomycin, baumycins A1 and A2, corresponding to Rf 0.27, 0.43 and 0.36, respectively, were determined by standard curve at 495 nm using a chromatoscanner (Shimazu TLC chromatoscanner, Model CS-910). Cultured medium after completion of the microbial conversion of exogenously added anthracyclinones, is centrifuged to separate mycelium from filtrate, and pigments are extracted from both filtrate and mycelium and purified as follows. To extract the products of the present invention, acetone, chloroform, methanol, butanol, toluene and acidic buffer solution can be used. Purification can be favorably carried out by adsorption and ion-exchange column chromatographies using silica gel (Wakogel C-200, Wako Junyaku), Sephadex LH-20 (Cross-linked dextran gels, Pharmacia Fine Chemical AB), and CM-cellulose (carbomethoxymethyl cellulose, Brown Co.). Physicochemical properties of daunomycin, baumycins A1 and A2 thus obtained in the present invention were determined by ultraviolet and visible absorption (abbreviated as UV), infrared absorption (IR), 100 MHz proton NMR (PMR) and mass spectral analyses, and coincided fully with the data published in J. American Chem. Society 86, 5334–5336 (1964) and J. Antibiotics 30, 619, 622 (1977).

The following examples are provided for illustrative purpose only and are not intended to limit the scope of the invention.

EXAMPLE 1

Process for producing daunomycin and baumycins A1 and A2 from aklavinone as a substrate.

A nutrient medium having the following composition were prepared:

| | |
|---|---|
| Soluble starch | 1.0% w/v |
| Glucose | 1.0% w/v |
| Soybean meal (ESSAN-M, special grade, Ajinomoto Co., Inc.) | 1.0% w/v |
| $KH_2PO_4$ | 0.1% w/v |
| $MgSO_4 \cdot 7H_2O$ | 0.1% w/v |
| $CuSO_4 \cdot 5H_2O$ | 0.0007% w/v |
| $FeSO_4 \cdot 7H_2O$ | 0.0001% w/v |
| $MnCl_2 \cdot 4H_2O$ | 0.0008% w/v |
| $ZnSO_4 \cdot 7H_2O$ | 0.00002% w/v |
| pH | 7.4 |

Three 500-ml Erlenmeyer flasks containing 100 ml of this sterilized medium were inoculated from an agar slant of *Streptomyces coeruleorubidus* ME130-A4, 1U-222 (FERM-P 5080) by platinum loop, and shake-cultured for 48 hours at 28° C. to produce a seed culture. Three hundred 500-ml flasks containing 50 ml of a previously sterilized medium consisting of 3% glucose, 1% meal, 2% corn steep liquor, 0.1% yeast extract, 0.3% NaCl, 0.2% $CaCO_3$ at pH 7.0 were respectively inoculated by 1 ml of the above seed culture, cultivated for 72 hours at 28° C. on a rotary shaker (220 rpm); then was added 1 ml of aklavinone solution (1 mg/ml in methanol) at the final concentration of substrate of 20 μg/ml in the flask, and the contents were cultivated further for 48 hours. Fifteen liters of the cultured medium thus obtained were centrifuged to separate the mycelium and filtrate, and the respective products were extracted and purified as follows. The products were extracted from the mycelium with 3 liters of acetone, and from the filtrate with 3 liters of chloroform. After the concentration of the acetone extract to one half volume under reduced pressure, pigments were reextracted twice with 2 liters of chloroform. The chloroform extracts from mycelium and filtrate were combined and concentrated under reduced pressure to obtain 13.8 g of oily substance. This oily substance was dissolved in 50 ml of chloroform and precipitated by adding 300 ml of n-hexane, and the resulting precipitate was dissolved in 150 ml of chloroform and extracted three times with 150 ml of 0.01 M acetate buffer to obtain an acid-soluble substance. The extract was adjusted to a pH of 8.5 with 2 M trishydroxyaminomethane solution, and reextracted three times with 150 ml of chloroform. The chloroform extract was concentrated to dryness under reduced pressure to obtain 430 mg of red powder. The crude powder was dissolved in 20 ml of chloroform-methanol mixture (20:1), transferred onto a silica gel column (100 g, 2×60 cm) prepared with chloroform-methanol (10:1) mixture, and eluted with the same mixture. After collecting the initial baumycin A1 fraction, baumycin A2 and daunomycin were eluted successively with 5:1 and 2:1 mixture of chloroform-methanol, respectively. The fractions corresponding to baumycins A1, A2 and daunomycin were respectively concentrated under reduced pressure, and applied to a Sephadex LH-20 column prepared with a toluene-methanol (3:1) mixture. Each respective eluate was concentrated, and n-hexane was added to the concentrate. The resulting red precipitate was filtered and dried in vacuo to obtain 46 mg of baumycin A1, 85 mg of baumycin A2 and 32 mg of daunomycin as pure red powders.

EXAMPLE 2

Process for producing daunomycin, baumycins A1 and A2 from ε-rhodomycinone as a substrate.

Using the same fermentation conditions and same size of production as in Example 1, ε-rhodomycinone instead of aklavinone was used for the microbial conversion. 20.3 g of crude oily substance were obtained from the mycelium and filtrate by extraction with acetone and chloroform according to the same extraction and isolation procedures in Example 1.

The crude substance was dissolved in 100 ml of chloroform and precipitated by adding 150 ml of n-hexane to obtain 18.4 mg of pigment. The pigment was dissolved in 200 ml of chloroform and transferred to 800 ml of 0.2 M sodium acetate buffer (pH 3.0) to obtain acid-soluble pigments. 0.5 M ethylenediaminetetraacetate was added to the acidic extract to be 0.01 M, and the solution was adjusted to a pH of 8.0 with 4 N NaOH, extracted three times with 300 ml of chloroform and concentrated to dryness. The resulting red powder (520 mg) was dissolved in 10 ml of chloroform-methanol (20:1) mixture transferred onto a silica gel column (80 g, 2.5×50 cm), and eluted with 8:1, 5:1 and 2:1 mixture of chloroform, successively. The respective fractions were collected, concentrated under reduced pressure, and chromatographed respectively on Sephadex LH-20 column (2×30 cm) prepared with toluene-methanol (3:1) mixture. The eluate from the above mixture was concentrated and precipitated by adding n-hexane to obtain 42 mg of baumycin A1, 55 mg of baumycin A2 and 28 mg of daunomycin.

EXAMPLE 3

Process for producing daunomycin and baumycins by addition of aklavinone or ε-rhodomycinone to the baumycin-producing culture.

As in Example 1, *Streptomyces coeruleorubidus* ME130-A4 was cultivated, fed with 100 μg/ml of aklavinone or ε-rhodomycinone, cultivated to complete bioconversion, and the products were purified according to Example 2. Thirty nine mg of daunomycin, 62 mg of baumycin A1 and 105 mg of baumycin A2 were obtained from the aklavinone feeding culture, and, on the other hand 43 mg of daunomycin, 112 mg of baumycin A1 and 58 mg of baumycin A2 were produced when ε-rhodomycinone was used.

What is claimed is:

1. A process for producing anthracycline antibiotics having the general formula I:

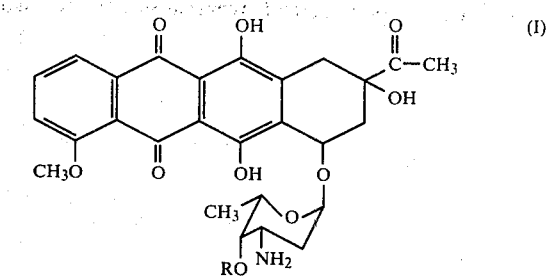

wherein
R represents a hydrogen atom or the acetal:

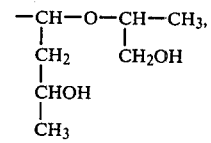

which comprises the microbial conversion by cultivating a microorganism of streptomyces, capable of converting an anthracyclinone selected from the group consisting of aklavinone and ε-rhodomycinone having the general formula II:

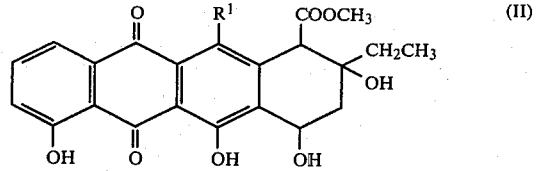

wherein
$R^1$ represents a hydrogen atom or a hydroxyl group, to the antibiotics daunomycin, baumycin A1 and baumycin A2, in an aqueous nutrient medium consisting of conventional carbon, nitrogen sources, inorganic salts and trace elements, and adding at least one of the said anthracyclinones into the cultured medium of said microorganism at the beginning stage of cultivation or during cultivation, and continuing the aerobic cultivation at 20° to 40° C. to complete the microbial conversion, and recovering said antibiotics from the cultured medium.

2. The process of claim 1 in which said microorganism is selected from the group consisting of *Streptomyces coeruleorubidus* ME130-A4 (FERM-P 3540), *Streptomyces peucetius* subsp. *carneus* ATCC 21354, *Streptomyces coeruleorubidus* ATCC 13740, *Streptomyces peucetius* NRRL B-3826 (FERM-P 3989) and their mutants capable of converting anthracyclinones having the general formula II to anthracycline glycosides having the general formula I.

3. The process of claim 1, wherein said anthracyclinone is aklavinone and said microorganism is *Streptomyces coeruleorubidus* (FERM-P 5080).

4. The process of claim 1, wherein said anthracyclinone is ε-rhodomycinone and said microorganism is *Streptomyces coeruleorubidus* (FERM-P 5080).

5. The process of claim 1, wherein said microorganism is *Streptomyces peucetius* subsp. *carneus* ATCC 21354.

6. The process of claim 1, wherein said microorganism is *Streptomyces coeruleorubidus* ATCC 13740.

7. The process of claim 1, wherein said microorganism is *Streptomyces peucetius* NRRL B-3826.

* * * * *